(12) United States Patent
Kubista

(10) Patent No.: US 6,876,954 B1
(45) Date of Patent: Apr. 5, 2005

(54) METHOD FOR CHARACTERIZING SAMPLES

(75) Inventor: Mikael Kubista, Nodro Solstensvägen (SE)

(73) Assignee: MultiD Analyses AB, Molnlyck (SE)

( * ) Notice: Subject to any disclaimer, the term of this patent is extended or adjusted under 35 U.S.C. 154(b) by 0 days.

(21) Appl. No.: 09/673,964

(22) PCT Filed: Aug. 14, 1998

(86) PCT No.: PCT/SE98/01468
§ 371 (c)(1),
(2), (4) Date: Dec. 19, 2000

(87) PCT Pub. No.: WO99/57543
PCT Pub. Date: Nov. 11, 1999

(30) Foreign Application Priority Data

Apr. 22, 1998 (SE) .............................................. 9801420

(51) Int. Cl.[7] ................................................. G06F 7/06
(52) U.S. Cl. ..................... 702/189; 702/179; 702/181; 702/190
(58) Field of Search ......................... 702/27, 179, 181, 702/189, 190, 194, 183, 19, 22, 23, 28, 29, 30–32, 76, 78, 134, 135, 172; 700/83; 703/2; 704/270; 356/487; 250/461.2; 708/33

(56) References Cited

U.S. PATENT DOCUMENTS

| 5,498,875 | A | | 3/1996 | Obremski et al. ........ 250/458.1 |
| 5,815,413 | A | * | 9/1998 | Hively et al. ................ 364/574 |
| 6,095,982 | A | * | 8/2000 | Richards-Kortum et al. ..... 600/476 |
| 6,246,481 | B1 | * | 6/2001 | Hill ............................ 356/487 |
| 6,351,712 | B1 | * | 2/2002 | Stoughton et al. ............. 702/19 |

FOREIGN PATENT DOCUMENTS

DE WO9531713 * 11/1995

OTHER PUBLICATIONS

Journal of Chemometrics, vol. 3, 1989, Bruce E. Wilson et al. "An Improved Algorithm For the Generalized Rank Annihilation Method", p. 493– p.498, whole document.*

* cited by examiner

Primary Examiner—Marc S. Hoff
Assistant Examiner—Felix Suarez
(74) Attorney, Agent, or Firm—Oppedahl & Larson LLP

(57) ABSTRACT

Physical samples are characterized to determine the content of the samples. A physical sample, or pair of physical samples, and the sample(s) are processed to generate a multidimensional response, calculating the 1-dimensional response of the components, to provide an indication of the content of the sample or samples. The multidimensional response may be measured by fluorescence or nuclear magnetic resonance.

14 Claims, 3 Drawing Sheets

METHOD FOR CHARACTERIZING SAMPLES

This application is a section 371 national phase application of PCT Application No. PCT/SE98/01468 filed Aug. 14, 1998.

Single test samples are characterized by generating multi-dimensional responses from which the components of the sample can be identified. The method does not require any references and is applicable even on samples which are less than the number of components they contain.

The present invention relates to methods for characterizing samples. These methods are i.a. used to investigate test samples from a production, patients or samples collected in any other way.

BACKGROUND OF THE INVENTION

When a sample is to be characterized for components, the components are generally separated from each other in a first step in order to identified and quantified in a later stage. However, it is not always possible to separate the components or it may not be motivated from a time/cost benefit reason. The samples may then be characterized spectroscopically whereby the components are identified by means of their unique spectral responses.

If one has a collection of samples and is aware of which components they comprise, it is, as a rule, trivial to determine their concentrations spectroscopically. This is due even if the spectral responses of the components overlaps each other. If, however, the components are unknown, the problem is muck more complicated. The situation was analysed for the first time in detail by the mathematics Lawton and Sylvestre (*Technometrics,* 13, 617, (1971)), who showed that it is impossible to find an unique solution even for a 2-component system. In 1990 we developed an experimental method, which partly solved this problem (Kubista, *Chemometrics and Intelligent Laboratory Systems,* 7, 273, (1990)). We then showed that if one carried out two spectroscopic measurements on each sample, in stead of one as previously used, and the measurements were such that the contribution of the components to these measurements had the same distribution of the intensities, but of different magnitude, then both the spectral responses as well as the concentrations of the components could be determined. Mathematically, these measurements are described using the equations:

$$A = CV \text{ or } a_j(\lambda) = \sum_{i=1}^{r} c_{ij} v_i(\lambda) \quad j = 1, 2 \ldots n$$

$$B = CDV \text{ or } b_j(\lambda) = \sum_{i=1}^{r} c_{ij} d_j v_i(\lambda) \quad j = 1, 2 \ldots n$$

wherein A is a matrix comprising spectra of the first type measured on the n samples; B is a matrix comprising spectra of the second type measured on the same n samples; C is a matrix comprising the concentrations of the r different components in the n samples; V is a matrix comprising the normalized spectra of the components; and D is a diagonal matrix, the r diagonal elements of which being the ratios between the responses of the components obtained in the two measurements. All spectra are digitalized in m points. We showed that the concentrations of the components (C), their normalized spectral responses (V) and the ratio between their responses obtained in the two measurements (D) could be determined only outgoing from the information obtained from the spectra as measured (A and B). We further described how the number of components of the samples (r) could be estimated.

One restriction using this method is that the number of components are not allowed to exceed the number of samples, which from a practical point of view means that the method can not be utilized on smaller series of samples and can not be applied on the whole for analysing isolated samples.

Several spectroscopic techniques, such as fluorescence, nmr, etc., can generate 2-dimensional data described by the equation:

$$I(\alpha, \beta) = \kappa \sum_{i=1}^{r} I_i(\alpha) c_i I_i(\beta)$$

where the signal. $I(\alpha,\beta)$, is determined as a function of two variables, $\alpha$ and $\beta$, and are the sum of the contribution of the components in each point, which contribution is proportional to their concentrations ($c_i$) and the products of their (normalized) 1-dimensional responses, $I_i(\alpha)$ and $I_i(\beta)$. Out of these responses the components can be identified. In a steady state fluorescence spectroscopy $I_i(\alpha)$ and $I_i(\beta)$ are the excitation- and emissions spectra of the components and are, as a rule, designated $I_i^{ex}(\lambda_{ex})$ and $I_i^{em}(\lambda_{cm})$, wherein $\lambda_{ex}$ and $\lambda_{cm}$ are the excitation and emission wavelengths. The shape of an excitation spectra of a pure compound is, in general independent of the emission wavelength used at the measurement, and the corresponding is due for its emission spectrum. The fluorescence signal monitored, if necessary after a correction for the inner filter effect (Kubista et al, *The Analyst,* 119, 417 (1994)), is proportional to the concentration of the compound. In a sample containing more compounds the total signal is the sum of the contribution by each component. As fluorescence is measured in an arbitrary unit, eq. 1 contains a proportionally constant ($\kappa$).

The information of the 2-dimensional spectrum $I(\alpha,\beta)$ is insufficient to unambiguously determine the spectral responses of the components. Different approximative ways have been suggested but these do not function sufficient satisfactorily even for a 2-component mixture (Burdik and Tu, *J. Chemometrics* 3, 431, (1989)).

The present invention is a method for analysing isolated test samples, or a couple of test samples without using references in such a way that the components can be identified.

BRIEF DESCRIPTION OF THE INVENTION

Figure 1:
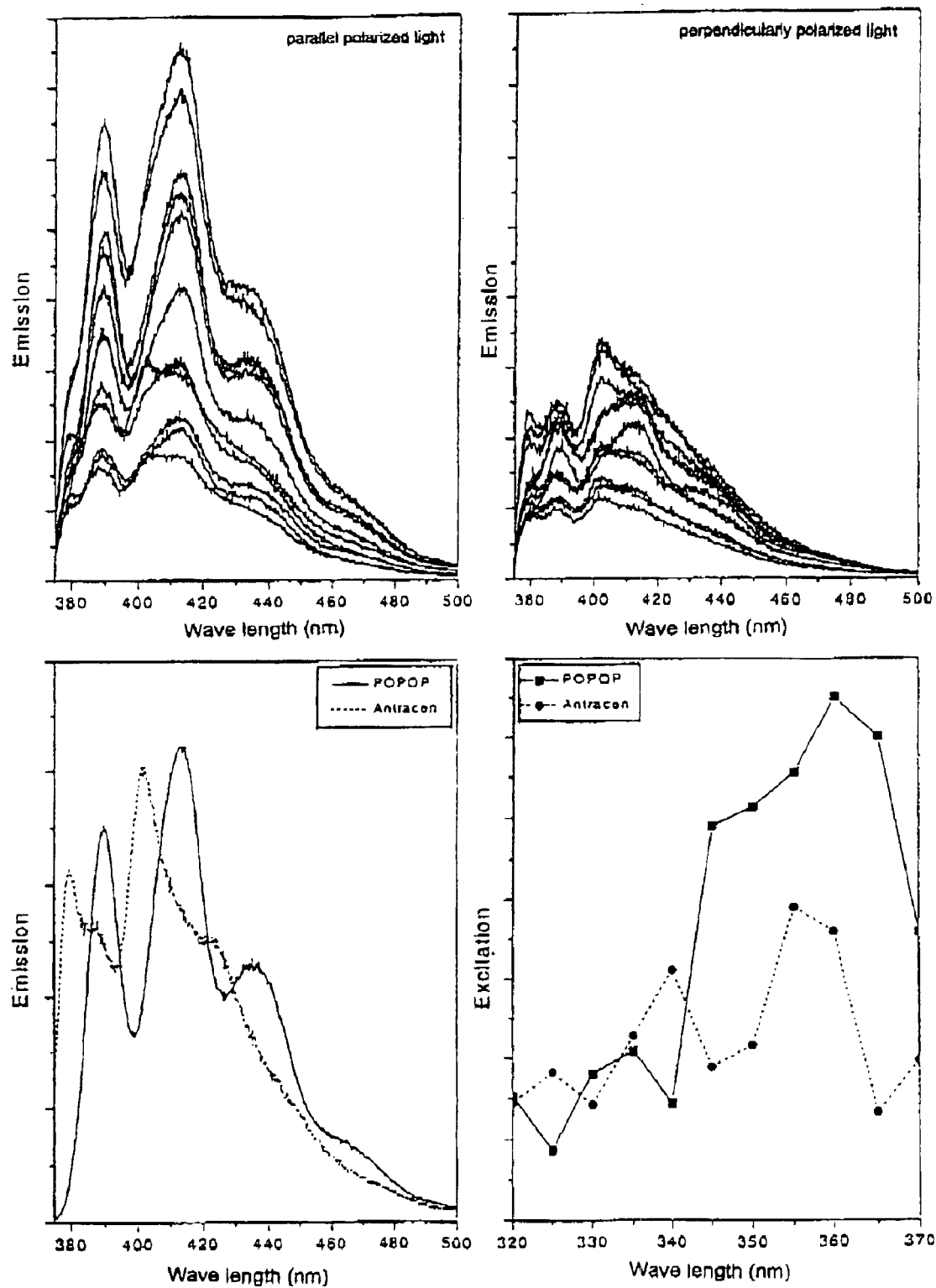
FIG. 1. Emission spectra monitored using different excitation wavelengths using a parallel polarized light (above, left) and a perpendicularly polarized light (above right), respectively. Down to the left the calculated emission spectra of the components are shown, and down to the right the calculated excitation spectra of the components are shown.

The present invention is a method for analyzing test samples in such a way that its components can be identified without the need for any reference data. The method is based upon the following four steps:

1. The test sample is analyzed using a method generating a 3-dimensional response according to:

$$I(\alpha, \beta, \gamma) = \sum_{i=1}^{r} \tilde{I}_i(\alpha)\tilde{I}_i(\beta)\tilde{I}_i(\gamma),$$

wherein r is the number of components contributing to the signal, and $\tilde{I}_i(\alpha)$ and $\tilde{I}_i(\beta)$ and $\tilde{I}_i(\gamma)$ are the arbitrarily normalized 1-dimensional responses of the components, which responses normally consist of spectral or concentration variations.

2. The number of components r as the sample contain is estimated.

3. For each component its 1-dimensional responses $I_i(\alpha)$ and $I_i(\beta)$ and $I_i(\gamma)$ are determined.

4. Out of the responses, the components are identified.

DETAILED DESCRIPTION OF THE PRESENT INVENTION

As the title indicates the present invention relates to a method for characterizing isolated test samples in a way that makes it possible to identify its components without any need for using reference samples. This is done through a strategic design of experiments which makes it possible to register a 3-dimensional response being proportional to the concentrations of the components, and the contribution from each component is the product of its specific 1-dimensional responses:

$$I(\alpha, \beta, \gamma) = \sum_{i=1}^{r} c_i I_i(\alpha) I_i(\beta) I_i(\gamma)$$

Such registration can be carried using certain forms of fluorescence spectroscopy, e.g., by means of a time disintegrated monitoring of emission/excitation spectra, i.e., the signal is registered as a function of excitation wavelength, emission wavelength, and time:

$$I(\lambda_{sx}, \lambda_{sm}, t) = \sum_{i=1}^{r} c_i I_i(\lambda_{sx}) I_i(\lambda_{sm}) I_i(t)$$

In these cases it is often suitable to gather the concentration of the components ci and the time declinations to a time dependent concentration:

$$I(\lambda_{sx}, \lambda_{sm}, t) = \sum_{i=1}^{r} c_i(t) I_i(\lambda_{sx}) I_i(\lambda_{sm})$$

The time can be time after light pulse (whereby $c_i(t)$ is proportional to the fluorescence declination), time after mixing of e.g., a stop-flow experiment (whereby $c_i(t)$ is the variation of the concentration of component i with time), time after treatment, such a photo bleaching (selective destruction of certain components using light), chromatographic or other form of separation, etc. At the analysis of such data the concentration variation of the components are calculated, as well as their excitation and emission spectra. It is of interest to note that intermediate components which are neither present at the beginning ($c_i(0)=0$) or at the end ($c_i(\infty)=0$) of the experiment can be identified from its calculated spectra.

There is a further possibility in varying the polarization of the light:

$$I(\lambda_{sx}, \lambda_{sm}, \alpha) = \sum_{i=1}^{r} c_i I_i(\lambda_{sx}) I_i(\lambda_{sm}) I_i(\alpha)$$

or, if the phase-modulated light is utilized, the frequency of the modulation:

$$I(\lambda_{sx}, \lambda_{sm}, \nu) = \sum_{i=1}^{r} c_i I_i(\lambda_{sx}) I_i(\lambda_{sm}) I_i(\nu)$$

etc.

There is further a possibility in varying the outer parameters which influences the concentrations of the components, such as temperature (pressure, volume, etc.):

$$I(\lambda_{sx}, \lambda_{sm}, T) = \sum_{i=1}^{r} c_i(T) I_i(\lambda_{sx}) I_i(\lambda_{sm})$$

or outer parameters which influence the intensity of the responses of the components, such as external magnetic fields (electrical fields, etc.):

$$I(\lambda_{sx}, \lambda_{sm}, M) = \sum_{i=1}^{r} c_i I_i(\lambda_{sx}) I_i(\lambda_{sm}) I_i(M).$$

The spectroscopic technique need not be a fluorescence technique. The method can be carried out using most techniques which generates 3-dimensional responses, e.g., nuclear magnetic resonance spectrometry (NMR) mass spectrometry, etc. It can further be carried out using most techniques generating 2-dimensional responses if the responses of the components influence external parameters. Finally, the method can be used using a technique generating 1-dimensional responses, as well, but then it is necessary that two external parameters are varied simultaneously and that their influence on the responses of the components are independent so that their contribution can be factorized.

The invention requests that at least two data points are determined in each of the 3 dimensions, i.e.:

$I_i(\alpha)$ wherein $\alpha_1, \alpha_2 \ldots \alpha_n$ $1 \leq 2$ $I_i(\beta)$ wherein $\beta_1, \beta_2 \ldots \beta_m$ $m \leq 2$ $I_i(\gamma)$ wherein $\gamma_1, \gamma_2 \ldots \gamma_1$ $n \leq 2$ To determine two data points only in all dimensions are, however, of particular meaning as the tolerance of the responses calculated then as a rule is insufficient to be able to identify the components. On the contrary it is quite excellent to have two data points only in one of the dimensions, e.g., l=2 (and m>>2, n>>2). This exhibits the advantage that the numerical treatment of data is made easier as the responses of the components can be calculated using fast algorithms such as Procrustes rotation and GRAM (Kubista, *Chemometrics and Intelligent Laboratory Systems* 7, 273, (1990); Wilson, Sanches & Kowalski, *J. Chemometrics*, 3, 493, (1989)). In the general case when all l, n, and m are greater than 2, the solution method is much more complicated and thus considerably more time consuming (Liwo, et al, *Computers Chem.*, 21, 89–91, (1997)). Furthermore, it is quite often of interest to carry out the experiment in such a way that one of m and n are considerably greater than the other. The reason hereto is that it as a rule, is sufficient for the identification of the components, to determine one of their 1-dimensional responses with a high accuracy.

The invention is not limited to determinations that generates 3-dimensional responses but even responses of a higher order can be used. In general it should be satisfying that the response is linear and that the contribution from each component shall be the product of its 1-dimensional responses:

$$I(\alpha, \beta, \gamma, \delta \ldots) = \sum_{i=1}^{r} c_i I_i(\alpha) I_i(\beta) I_i(\gamma) I_i(\delta) \ldots$$

Of course, the higher the dimension is the more time consuming the numerical treatment of the determined data will become. However, with regard to the vary fast development within the computer area this will hardly be a practical limitation in the future.

The samples to be analysed shall contain substantially the same components, and these shall be present in different, relative concentrations. The samples are analysed in pair using a 2-dimensional method which provides a response which is proportional to the concentrations of the components and the product of the 1-dimensional responses. This can be expressed as:

$$I^A(\alpha, \beta) = \sum_{i=1}^{r} I_i(\alpha) c_i^A I_i(\beta)$$

$$I^B(\alpha, \beta) = \sum_{i=1}^{r} I_i(\alpha) c_i^B I_i(\beta)$$

wherein $I^A(\alpha)$ and $I_B(\beta)$ are spectra of the two samples which in the following will be called A and B, determined as a function of the variables $\alpha$ and $\beta$, r is the total number of components contributing to the spectra, $I_i(\alpha)$ and $I_i(\beta)$ are the normalized 1-dimensional responses of the components, $c_i^A$ and $c_i^B$ are their concentrations, respectively. In a steady-state fluorescence spectroscopy $I_i(\alpha)$ are the normalized excitation spectra of the components, $I_i^{ex}(\lambda_{ex})$, and $I_i(\beta)$ are their normalized emission spectra, $I_i^{em}(\lambda_{em})$:

$$I^A(\lambda_{sx}, \lambda_{sm}) = \sum_{i=1}^{r} I_i^{sx}(\lambda_{sx}) c_i^A I_i^{sm}(\lambda_{sm})$$

$$I^B(\lambda_{sx}, \lambda_{sm}) = \sum_{i=1}^{r} I_i^{sx}(\lambda_{sx}) c_i^B I_i^{sm}(\lambda_{sm})$$

The information in these spectra is treated in two steps. First the number of components, r, is determined, and then the 1-dimensional responses of the components, $$I_i^{ex}(\lambda_{ex}), \text{ and } I_i^{am}(\lambda_{tm}).$$

When r has been determined, the spectral responses of the components. The equations:

$$I^A(\lambda_{sx}, \lambda_{sm}) = \sum_{i=1}^{r} I_i^{sx}(\lambda_{sx}) c_i^A I_i^{sm}(\lambda_{sm})$$

-continued $$I^B(\lambda_{sx}, \lambda_{sm}) = \sum_{i=1}^{r} I_i^{sx}(\lambda_{sx}) c_i^B I_i^{sm}(\lambda_{sm})$$

can be written in matrix form as:

$A = XC^A M$ $B = XC^B M$ wherein A and B are matrixes comprising the spectra determined, X is a matrix comprising the normalized excitation spectra of the components, M is a matrix comprising their normalized emission spectra, and $C^A$ and $C^B$ are diagonal matrixes comprising the concentrations of the components. By renormalizing one of X or M, the equation system can be rewritten as:

$A = XM$ $B = XDM$ wherein D is a diagonal matrix comprising the ratios between the concentrations of the components ($D = C^B/C^A$). Using A and B, X, M and D can be calculated using known methods such as Procrustes rotation (Kubista, *Chemometrics and Intelligent Laboratory Systems*, 7, 273, (1990); and GRAM (Wilson, Sanches & Kowalski, *J. Chemometrics*, 3, 493, (1989).

As a summary, the present invention relates to a method for experimentally studying two samples spectroscopically so that the information present in the experimental spectra is sufficient to determine the number of components of the samples (r), their spectral responses of the 1$^{st}$ dimension, $I_i(\alpha)$, their spectral responses of the 2$^{nd}$ dimension, $I_i(\beta)$, and the ratios between their concentrations ($c_i^A/c_i^B$).

The most apparent use of the invention is for the analysis of two samples containing common components. All components need not be common, but the majority of those contributing spectroscopically should be in common (Booksh & Kowalski, J. Chemotrics, 8, 287, (1994)). The number of components is arbitrary and can exceed 2.

Another use of the invention is to characterized single samples by first dividing them into two part samples containing the ingoing components is different proportions. This can be accomplished in several ways, e.g., by filtering, extracting, chromatographing dialysing, centrifuging, precipitating, splitting the sample by means of an electric field, etc. Alternatively, the original sample can be used as one sample, and an aliquot thereof, which is created in such a way that the components are present in other proportions, is used as the second sample, This aliquot can be obtained by selectively eliminating certain components, e.g., by means of adsorption, precipitation, freezing, distillation, selective decomposing (e.g., by light, heat, radio lysis), etc. Another possibility is to create two samples from one, is to change the conditions for the determination, e.g., by changing the temperature, pressure, etc. Separation methods, such as different types of chromatography are of interest, as the components are separated in space, and one, principally arbitrary number of samples can be obtained which can be analysed in pair. Using spectroscopic techniques which generates 2-dimensional spectra in a fast way, then, furthermore, the detection can be made on-line.

Another use of the invention is to determine the concentration of the components in one test sample in relation to a standard sample with a high degree of accuracy. The standard sample and the test sample are analysed as a pair, and the ratio between the concentrations of the components is obtained as the diagonal element of the D matrix.

2-dimensional spectra wherein one of the dimensions is time, are of particular interest, whereby time is related to time after a disturbance such as a relaxation time. Today, there are e.g., fluorescence instruments by means of which one can determine complete spectra as a function of time after lightening (either directly after lightening using a light pulse, or indirectly using phase modulation technique). This gives using α as time, and β as wave length, the equation system:

$$I^A(t, \lambda) = \sum_{i=1}^{r} I_i(t) c_i^A I_i(\lambda)$$

$$I^B(t, \lambda) = \sum_{i=1}^{r} I_i(t) c_i^B I_i(\lambda)$$

from which r, $I_i(t)$, $I_i(\lambda)$ and $(c_i^A/c_i^B)$ can be determined.

EXAMPLE

The invention will be further illustrated in four examples.

Example 1

A sample is characterized using fluorescence spectroscopy, where excitation wave length, emission wave length, and light polarization are varied (FIG. 1). This gives raise to a 3-dimensional spectrum according to:

$$I(\lambda_{sx}, \lambda_{sm}, \alpha) = \sum_{i=1}^{r} c_i I_i(\lambda_{sx}) I_i(\lambda_{sm}) I_i(\alpha)$$

In the example 650 different emission wave lengths (m), 11 different excitation wave lengths (n) and 2 different polarizations (α=0o, called parallel polarization, and α=90o, called perpendicular polarization (I), are used. From the response determined, $In(\lambda_{ar}, \lambda_{cm}, \alpha)$, first the number of components (r) is estimated to 2 (using a statistic test and a visual inspection of the principal components). Then the component specific responses are calculated. For this purpose one uses the fact they only two data points were registered in one of the dimensions (polarization) and rewrote the 3-dimensional response to two 2-dimensional response.

$$I(\lambda_{sx}, \lambda_{sm}, \alpha = 0°) = \sum_{i=1}^{r} c_i I_i(\lambda_{sx}) I_i(\lambda_{sm}) I_i(\alpha = 0°)$$

$$I(\lambda_{sx}, \lambda_{sm}, \alpha = 90°) = \sum_{i=1}^{r} c_i I_i(\lambda_{sx}) I_i(\lambda_{sm}) I_i(\alpha = 90°)$$

These can be described using the equation system:
$I^0 = X\alpha^0 M$
$I^{90} = X\alpha^{90} M$
which can be solved using Procrustes rotation (Kubista, *Chemometrics and Intelligent Laboratory Systems*, 7, 273 (1990)). This gave the normalized excitation intensities of the components as matrix $X(I_i(\lambda_{ex}))$, (shown down to the right in FIG. 1), the normalized emission intensities of the components as matrix $M(I_i(\lambda_{cm}))$ (shown down to the left in FIG. 1), and the ratios between the responses of components to light of different polarization From the calculated component specific responses, in particular the emission spectra, the component could be identified as p-bis[2-(5-phenyloxazolyl)]-benzene (POPOP), and antracene. Finally, by comparing standard spectra of POPOP and antracene the concentrations could be estimated to some micro molars.

Example 2

Two solutions containing the dye compounds POPOP, dimethyl POPOP, antracene and diphenyl antracene in different proportions were prepared. On these fluorescence excitation spectra were monitored a several emission wave lengths. The number of components were determined to 4 using a statistic test, and the excitation spectra of the components (FIG. 1), emission intensities and the relation between their concentrations in the two samples were calculated.

Example 3

Figure 2:
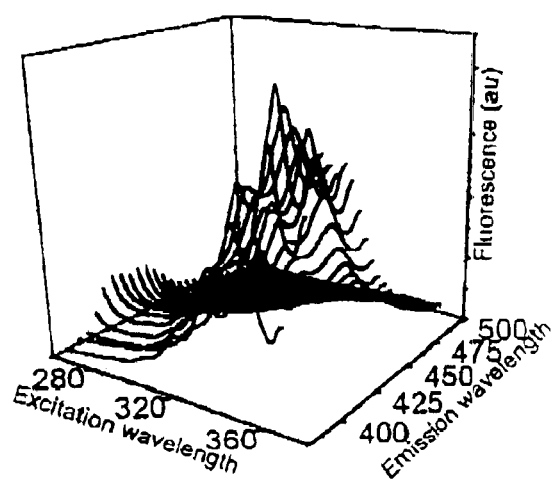
FIG. 2. A) Excitation spectra registered using different emission wavelengths from two solutions containing POPOP, dimethyl POPOP, antracene, and diphenyl antracene. B) The excitation spectra of the components is calculated.
Figure 2:
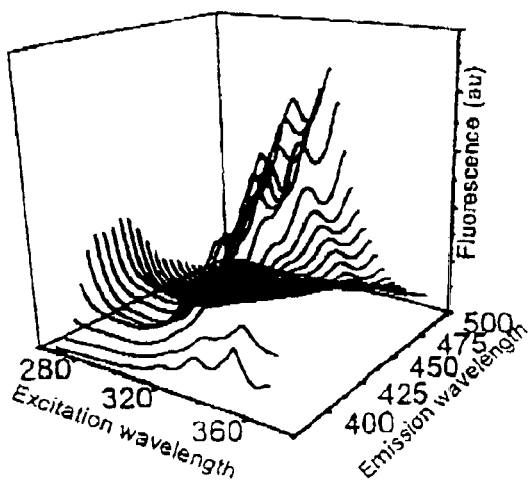
Figure 2:
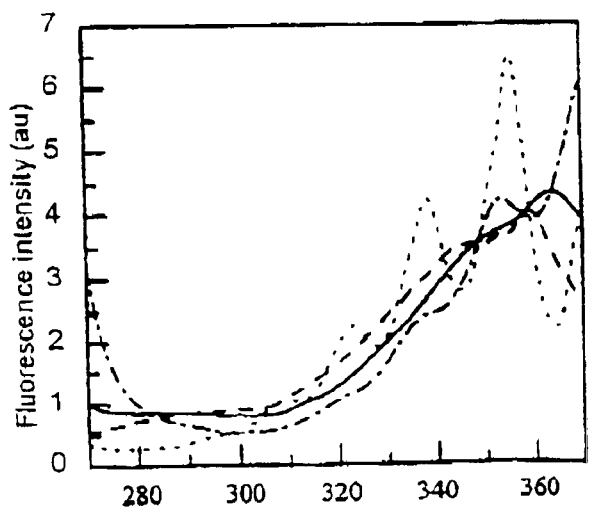
Figure 3:
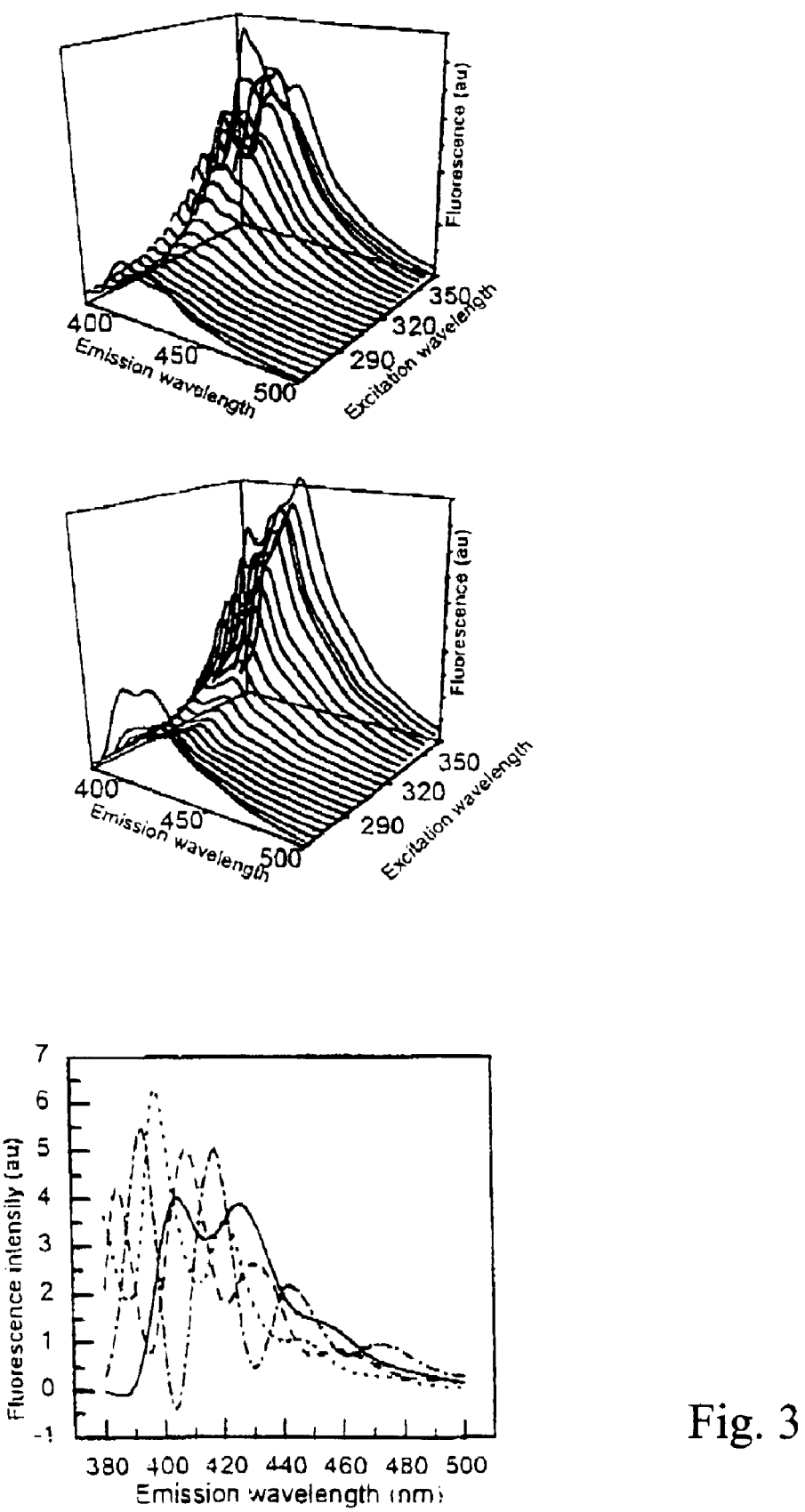
FIG. 3. A) Emission spectra registered using different excitation wavelengths of two solutions POPOP, dimethyl POPOP, antracene, and diphenyl antracene. B) The excitation spectra of the components as calculated.

On the same solutions as in Example 1 the fluorescence emission spectra were monitored using a number of excitation wave lengths. The number of components were determined to 4 using a statistic test, and the emission spectra of the components (FIG. 2), excitation intensities and the relation between their concentrations in the two samples were determined.

Example 4

Characterization of samples containing the dye compound thiazole orange and the polymer poly(dG) was made. The samples were analysed in pairs using 2-dimensional fluorescence spectroscopy. They contains thiazole orange and poly(dG) in the relation [thiazole orange]/[poly(dG)] of 0.05 and 0.025. Neither poly(dG) nor the dye compound is fluorescentic as such but the fluorescence arises when thiazole orange binds to the polymer. The samples were analysed in two different ways. In one analysis, the fluorescence excitation spectra were monitored at different emission wave lengths. The number of fluorescent components were identified to two using statistic tests, and their excitation spectra and emission intensities were calculated. In the second analysis, the fluorescence emission spectra were monitored using a number of excitation wave lengths. Once again the number of components was identified to two, and their emission spectra and excitation intensities were calculated.

What is claimed is:

1. A method for characterizing physical samples to determine the content of the samples comprising the steps of:

obtaining a physical sample, or pair of physical samples, processing the sample or samples to generate a multidimensional response according to $$I(\alpha, \beta, \gamma, \ldots) = \sum_{i=1}^{r} c_i I_i(\alpha) I_i(\beta) I_i(\gamma) \ldots$$

where the number of data points in each dimension are at least two $\alpha_1, \alpha_2 \ldots \alpha_l \quad l \leq 2$
$\beta_1, \beta_2 \ldots \beta_m \quad m \leq 2$
$\gamma_1, \gamma_2 \ldots \gamma_n \quad n \leq 2$ and calculating the 1-dimensional responses of the components, $\tilde{I}_i(\alpha), \tilde{I}_i(\beta), \tilde{I}_i(\gamma) \ldots$ to provide an indication of the content of the sample or samples.

2. The method according to claim 1, wherein the number of samples is two and these are analyzed using a method generating a 2-dimensional response according to $$I(\alpha, \beta) = \sum_{i=1}^{r} I_i(\alpha) c_i I_i(\beta)$$

and the 1-dimensional responses of the components and the ratios between their concentrations in the two sample, ($c_i^B/c_i^A$) are calculated by solving the equation system:

$$I^B(\alpha, \beta) = \sum_{i=1}^{r} I_i(\alpha) c_i^B I_i(\beta).$$

3. The method according to claim 2, wherein the two samples are generated from one sample.

4. The method according to claim 2, wherein one of the samples is used as standard sample to determine the concentrations of the components in a test sample.

5. The method according to claim 1, wherein a single sample is analyzed using a technique generating a 3-dimensional response $$I(\alpha, \beta, \gamma) = \sum_{i=1}^{r} c_i I_i(\alpha) I_i(\beta) I_i(\gamma).$$

6. The method according to claim 1, wherein a single sample is analyzed using a technique generating a 2-dimensional response simultaneously as environmental conditions are varied in such a way that the concentration of the components are changed in time:

$$I(\alpha, \beta, t) = \sum_{i=1}^{r} c_i(t) I_i(\alpha) I_i(\beta).$$

7. The method according to claim 1, wherein exactly two data points are collected in one of the dimensions.

8. The method according to claim 1, wherein the multi-dimensional response is measured by fluorescence or nuclear magnetic resonance.

9. The method according to claim 8, for characterization a test sample by analyzing time dependent spectra, wherein the time relates to time after irradiation, time after mixing of components, time after changing environmental conditions, or time after initiation of separation.

10. The method according to claim 8, wherein the test sample is characterized by analyzing two time dependencies, in combination with at least some other dependency selected from the group consisting of energy, wavelength or frequency of radiation.

11. The method according to one or more claims 1, wherein the variations along, at least one of the dimensions, is obtained by varying time, electric, magnetic or electromagnetic field, temperature, frequency modulation or polarization.

12. The method according to claim 11 for characterization a test sample by analyzing time dependent spectra, wherein the time relates to time after irradiation, time after mixing of components, time after changing environmental conditions, or time after initiation of separation.

13. The method according to claim 11, wherein the test sample is characterized by analyzing two time dependencies, in combination with at least some other dependency selected from the group consisting of energy, wavelength or frequency of radiation.

14. The method according to claim 1, wherein the response monitored is broken down to an orthogonal basset e.g., using a principal component division, the number of components (r) in the sample is estimated, and the arbitrary normalized 1-dimensional responses of the components are calculated.

* * * * *